(12) United States Patent
Ruimi

(10) Patent No.: US 7,016,453 B2
(45) Date of Patent: Mar. 21, 2006

(54) INTERVENTIONAL COMPUTERIZED TOMOGRAPHY SYSTEM WITH REDUCED PHYSICIAN EXPOSURE

(75) Inventor: David Ruimi, Netania (IL)

(73) Assignee: Koninklijke Philips Electronics N.V., Eindhoven (NL)

(*) Notice: Subject to any disclaimer, the term of this patent is extended or adjusted under 35 U.S.C. 154(b) by 204 days.

(21) Appl. No.: 10/399,242

(22) PCT Filed: Jan. 18, 2001

(86) PCT No.: PCT/IL01/00047

§ 371 (c)(1),
(2), (4) Date: Apr. 15, 2003

(87) PCT Pub. No.: WO02/056771

PCT Pub. Date: Jul. 25, 2002

(65) Prior Publication Data

US 2004/0068171 A1    Apr. 8, 2004

(51) Int. Cl.
*A61B 5/05* (2006.01)

(52) U.S. Cl. .................... 378/4; 378/16; 378/114; 378/116

(58) Field of Classification Search ........... 378/206, 378/205, 196, 197, 4, 19, 42, 15, 16, 114, 378/117, 145
See application file for complete search history.

(56) References Cited

U.S. PATENT DOCUMENTS

| 5,265,610 A | 11/1993 | Darrow et al. |
| 5,873,826 A * | 2/1999 | Gono et al. ............... 600/425 |
| 6,435,717 B1 * | 8/2002 | Kohler et al. .............. 378/206 |
| 6,501,820 B1 * | 12/2002 | Guendel .................... 378/15 |

FOREIGN PATENT DOCUMENTS

| EP | 0 545 588 | 6/1993 |
| EP | 0 819 407 | 1/1998 |
| EP | 0 860 144 | 8/1998 |
| EP | 0 872 227 | 10/1998 |
| WO | WO 98/36690 | 8/1998 |

* cited by examiner

Primary Examiner—Edward J. Glick
Assistant Examiner—Irakli Kiknadze

(57) ABSTRACT

A CT system for use in interventional procedures on a patient (20) supported by a support surface (24). The system includes a normal mode in which a patient is irradiated over an angle including irradiation from a general direction above the support surface, and a reduced angle irradiation mode in which the patient is irradiated only from an angle at which a physician is indicated as not being present or is assumed not to be present.

20 Claims, 5 Drawing Sheets

INTERVENTIONAL COMPUTERIZED TOMOGRAPHY SYSTEM WITH REDUCED PHYSICIAN EXPOSURE

RELATED APPLICATIONS

This application is a U.S. national filing of PCT Application No. PCT/IL01/00047, filed on Jan. 18, 2001.

FIELD OF THE INVENTION

The present invention is related to the field of interventional medical procedures, such as biopsy procedures, utilizing computerized tomography (CT) images and especially to systems that reduce the radiation exposure of the physician.

BACKGROUND OF THE INVENTION

Interventional procedures that are aided by images acquired during the procedures are well known. Such procedures have been reported utilizing almost every imaging modality. When taking biopsies, for example, a biopsy needle path is determined from an image of the region. During the insertion of the needle new or updated images are acquired and displayed to the physician to assure that the path is being followed or to allow for changes in the path as necessary.

For some procedures, especially those for which very accurate determination of needle path and position is necessary (for example, for brain biopsies) CT is an imaging modality of choice, since it provides superior and accurate representations of structure.

PCT publication WO 98/36690 describes a method and apparatus for efficiently producing updated images during an intervention procedure. Many other patents and other publications deal with CT systems useful for biopsy and other procedures.

However, despite the fact that such procedures are available on or easily implemented on existing CT imagers, they are not popular with physicians, apparently because the physicians hand (at least) is exposed to radiation during the procedure.

SUMMARY OF THE INVENTION

A general aspect of the invention is the provision of updated CT images during an interventional procedure, such as a biopsy, while reducing the amount of radiation to which the physician is exposed.

According to some exemplary embodiments of the invention, data is acquired utilizing positions of the x-ray source that do not directly irradiate the physicians body. Since for efficient and speedy reconstruction it is generally desirable to irradiate the patient over at least a 180 degree angle, it is generally impossible to completely avoid also irradiating the physician to some extent. However, in accordance with exemplary embodiments of the invention, the direction of irradiation is chosen such that the body of the physician is on the other side of the patent's body from the x-ray source. Since the patient's body absorbs most of the irradiation incident on it, the irradiation of the physician is greatly reduced.

In accordance with some embodiments of the invention, the irradiation positions during an interventional procedure are chosen without reference to the position of the biopsy itself. This is possible since the biopsy is always performed from above (with respect to the patient support) for obvious reasons. Thus, utilizing the simple expedient of irradiating only from below (and optionally additionally from an acute angle on each side of the horizontal) is sufficient to avoid direct irradiation of the physician in most cases.

Alternatively, after planning of the interventional procedure, when the position and direction of entry into the patient is known, the angles of irradiation are specifically chosen to avoid direct irradiation of the physician. Using this method, one or both of a wider angle of views or optimally low irradiation of the physician (or a trade-off between them) can be achieved.

In accordance with some embodiments of the invention, the reduced and specific angles of irradiation are utilized during the entire procedure. That is, as soon as the procedure starts (and optionally even before the procedure starts) the angles of irradiation are restricted, in the manner described above. Alternatively, the angles are restricted only when there is an indication of the presence of the physicians body in the radiation field. Such indication may be mechanical, activated by a switch (such as a foot switch) pressed by the physician.

Alternatively, provision is made for automatically determining the presence of a part of the physicians body, in the field of view of the x-ray irradiation. Such determination can be made in many ways, including optical trip wires or by analysis of images acquired by the CT imager. Analysis of the raw acquired data and/or the data after convolution can also identify the presence and at least the angular position of the physician in the filed. It should be understood that, when analysis of the image is call for herein, the method also includes analysis of the raw data and/or of the prep data.

When the imager is used to determine the presence of the physician in the field of view, the images are analyzed to detect the introduction of a portion of the physician's body into the field of view (for example by determining that an object has entered the filed of view, outside the body of the patient). When the presence of the physician in the field of view is detected, the angles at which the x-ray tube irradiates are restricted as aforesaid. Optionally, when the physician's body is removed from the field of view (as determined by the detector), the restriction on the irradiation angles is removed to improve the quality of the acquired images.

Optionally, The detector may determine not only the presence of the physicians body in the field by also its position. The irradiation angles can then be optimized to provide an irradiation segment that avoids the direct irradiation of the physician. Optionally, the irradiation angle is fixed and only its position changes. Alternatively, the angle is also adjusted responsive to the position determination.

There is thus provided, in accordance with an exemplary embodiment of the invention, a CT system for use in interventional procedures on a patient supported by a support surface, having:

a normal mode in which a patient is irradiated over an angle including irradiation from a general direction above the support surface; and a reduced angle irradiation mode in which the patient is irradiated only from angle at which a physician is indicated as not being present or is assumed not to be present.

Optionally, the normal mode comprises irradiation of the patient mainly from beneath the support. Optionally, the normal mode also includes irradiating the patient from at least one side, to an extent necessary to acquire complete sets of data for image reconstruction.

In an embodiment of the invention, the reduced angle irradiation is based on a known intervention direction.

In an embodiment of the invention, the system includes at least one presence detector operative to detect the presence of a person other than the patient in the field of the imager and the CT system switches from, the normal mode to the reduced angle mode based on said detection.

Optionally, the presence detector comprises analysis circuitry that analyzes CT images acquired by the imager, raw data acquired by the imager and/or projection data.

In an embodiment of the invention, the presence detector comprises a source and a detector, wherein said presence is indicated based on a change in a signal produced by said detector.

In an embodiment of the invention the presence detector comprises a physical indicator operated by an operator that switches the CT system between said modes.

In an embodiment of the invention, the presence detector also determines a position of the other person in the CT field. Optionally, the system includes a controller that receives the position information and controls the extent of the reduced angle responsive to the position information.

In an embodiment of the invention, the normal mode comprises irradiating the patient over a 360 degree angle.

BRIEF DESCRIPTION OF THE DRAWINGS

Exemplary embodiments of the invention are described with reference to the following drawings. Similar or identical elements present in more than one drawing are denoted by the same or similar reference numbers.

DETAILED DESCRIPTION OF EXEMPLARY EMBODIMENTS

Figure 1:
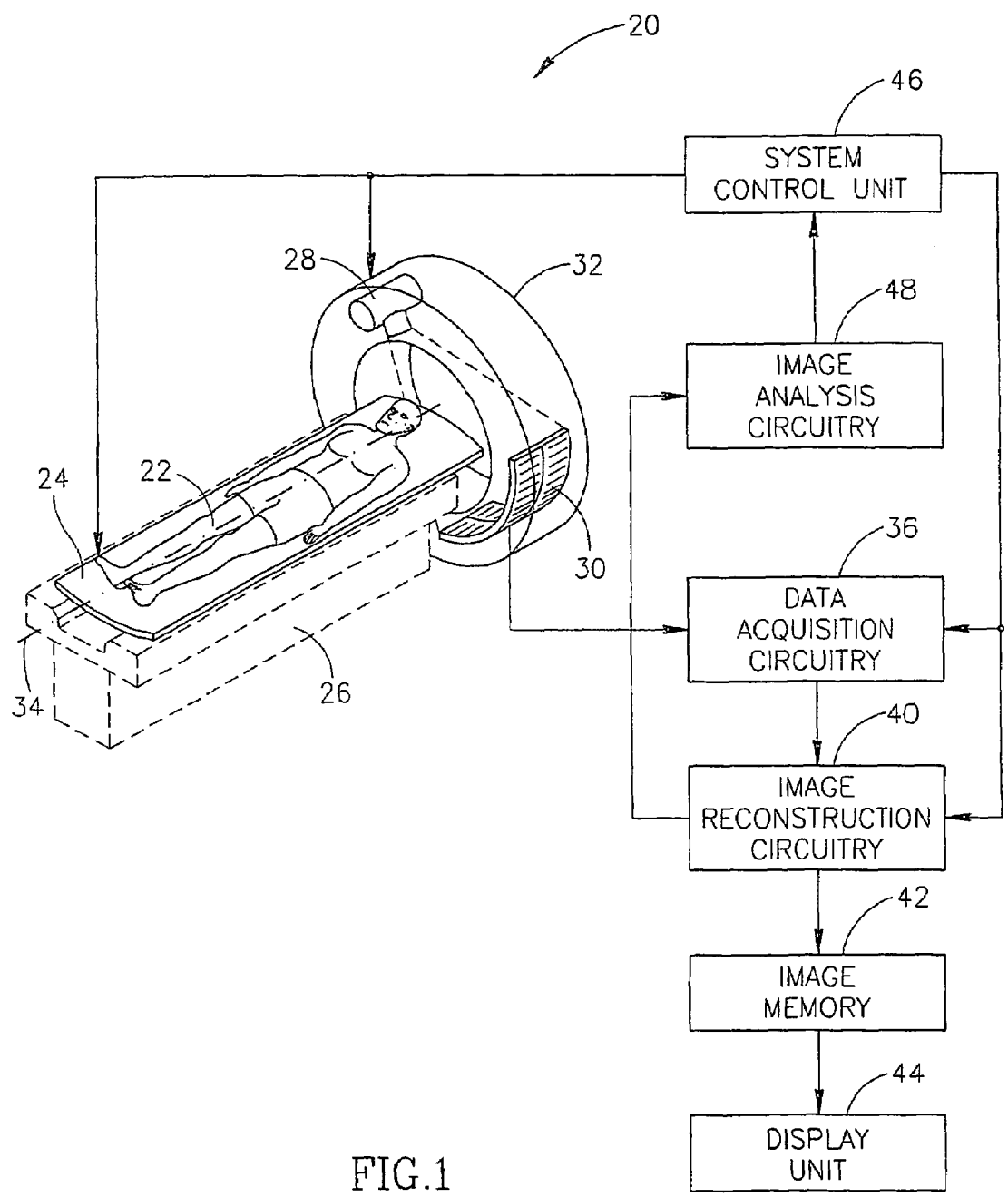
FIG. 1 shows a schematic perspective view of a CT imager, in accordance with an exemplary embodiment of the invention.

FIG. 1 shows a third generation CT scanner 20, for scanning a patient 22, fitted with various accessories in accordance with an embodiment of the invention. While a third generation system is shown, first, second or fourth generation systems or systems utilizing a ring x-ray source can be used in other embodiments of the invention.

Scanner 20 comprises a patient support system 36 on which a table 24 is mounted. An axis 34 of the CT scanner is also shown. An x-ray tube 28 emits a fan beam that irradiated a portion of patient 22. Irradiation that passes through the patient is detected by one or more rows 30 of detectors.

A system control unit 46 controls rotation of the tube and detectors. In normal operation, the control unit also controls movement of table 24 such that individual slice or helix data, as well known in the art, is acquired. Image reconstruction circuitry 40 reconstructs slices from the data acquired and stores it in an image memory 42. Images can be displayed on a display unit 44.

Under normal imaging conditions, tube 28 and detectors 30 rotate around the patient and emit radiation (and acquire data) over the entire rotation.

In some embodiments of the invention, the system includes image analysis circuitry 48 that receives the images from image reconstruction circuitry 40 and determines whether a substantial object is introduced into the field of view of the CT imager outside the patient's body. As a preliminary matter, the patients body is preferably, but not necessarily, first imaged by the CT imager as a reference for the detection of the insertion of the object.

In an embodiment of the invention when an object is detected, it is assumed to be a portion of the physician's body and the radiation is emitted over a reduced portion of the rotation.

Methods for determining the extent of the portion of the rotation during which radiation is emitted are discussed below.

Figure 2:
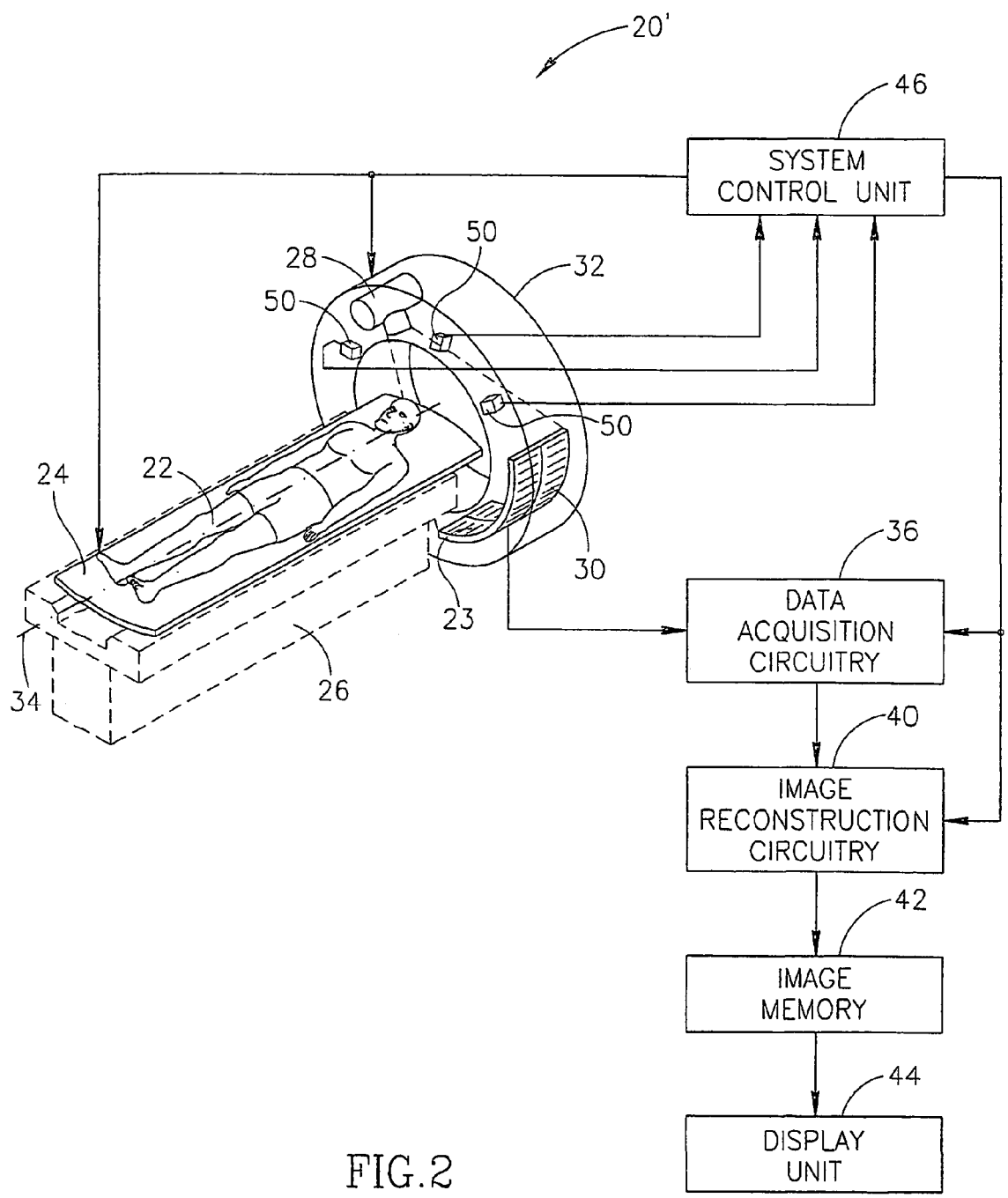
FIG. 2 shows a schematic perspective view of an alternative CT imager in accordance with an embodiment of the invention.

FIG. 2 shows an alternate CT imager 20'. This imager is identical with imager 20, except that image analysis circuitry 48 is replaced by a series of presence detectors, shown schematically at 50. These presence detectors can be, for example, laser sources and laser detectors, which determine if there is anything present between the laser sources and laser detectors. Thus, the presence of a portion of the physician's body between a particular laser source and laser detector would result in an indication to controller 46 that the physician is in the radiation field and trigger the reduced angle irradiation. Optionally, other presence detectors as known in the art may be used.

Alternatively, the presence of the physician can be indicated to controller 46 directly by the physician (or other person) by pressing a button or a foot-pedal (not shown). Such indication may be continuous, such that as long as the pedal or button is pushed the radiation directions are reduced. Alternatively, and preferably, one press on the pedal or button reduces the irradiation angle and a second resets it to the fall 360 degrees. Optionally, an indicator light (not shown), sound or other indicator indicates the irradiation mode to the physician. Alternatively, the reduced angle scheme is initiated by using a special irradiation protocol in the CT scanner, used for the entire procedure.

In accordance with various embodiments of the invention, several different schemes for reduced angle irradiation are possible. A particular CT imager may have one or more schemes available.

The simplest methodology utilizes a fixed irradiation profile, independent of the actual position of the physicians body. This scheme utilizes the fact that the physicians body is present only above the patient and not below the patient. Thus, under this scheme, when reduced irradiation angle is indicated the irradiation is turned on only-when the source is below the table line, plus optionally, several degrees above the line, if required to acquire a complete data set for reconstruction. For other configurations of CT scanner, other positions at which the physician is not present may be known.

When the side of the table at which the physician is standing is known, the angles may be changed or expanded to take into account that the physician is not present on the other (lateral) side of the patient. This may be known to the system from an indication inputted to the controller by the physician (for example via display/interface 44 to controller 46), from knowledge of the plan for insertion of a catheter or biopsy needle (see below) or from image analysis circuitry 48 or detectors 50 which may determine the position of the physician's hand or of a biopsy needle.

Figure 5:
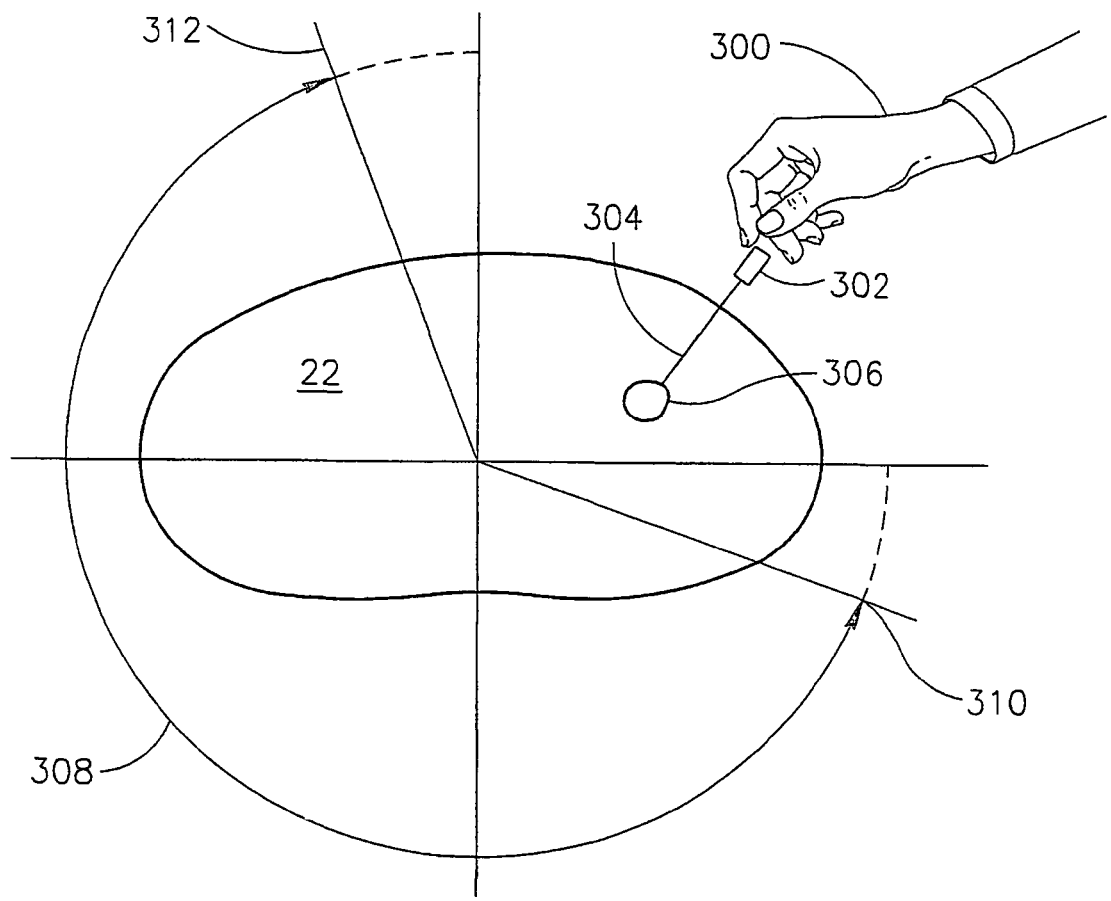
FIG. 5 shows a typical irradiation profile, in accordance with an exemplary embodiment of the invention.

A typical irradiation scheme for an insertion based protocol or where the position of the physician is shown is shown in FIG. 5. In FIG. 5 a physician's hand 300 is shown near an insertion point 302 in an insertion path 304 to a lesion 306. For this case, considering an x-ray tube path as shown at 308, the x-rays are turned on at point 310 and turned off at 312, so that the physician is not directly irradiated.

Alternatively, the irradiation scheme is dynamically determined based on indications of the actual position of the physicians body within the field of the CT imager. Such indications may come, for example, from image analysis circuitry 48 or detectors 50. With such knowledge controller 46 determines a safe angular spread of irradiation positions, based on substantially instantaneous knowledge of the position of the physician's body within the field.

Alternatively, the position of the physician is determined from knowledge of the direction of insertion of a biopsy needle or the like. Traditionally, the path of such a needle is first mapped on a previously acquired CT acquisition. During the procedure, the actual path of the needle is compared to the planned path so that corrections can be made to assure reaching the lesion being biopsied or treated and to avoid damage to the patient during the insertion. When the direction of insertion is known, the controller is programmed to provide irradiation only from angle at which the physician is not directly irradiated. The reduced angle irradiation may be initiated only when the physician is in the irradiation region or may be constant during the entire procedure.

Figure 3:
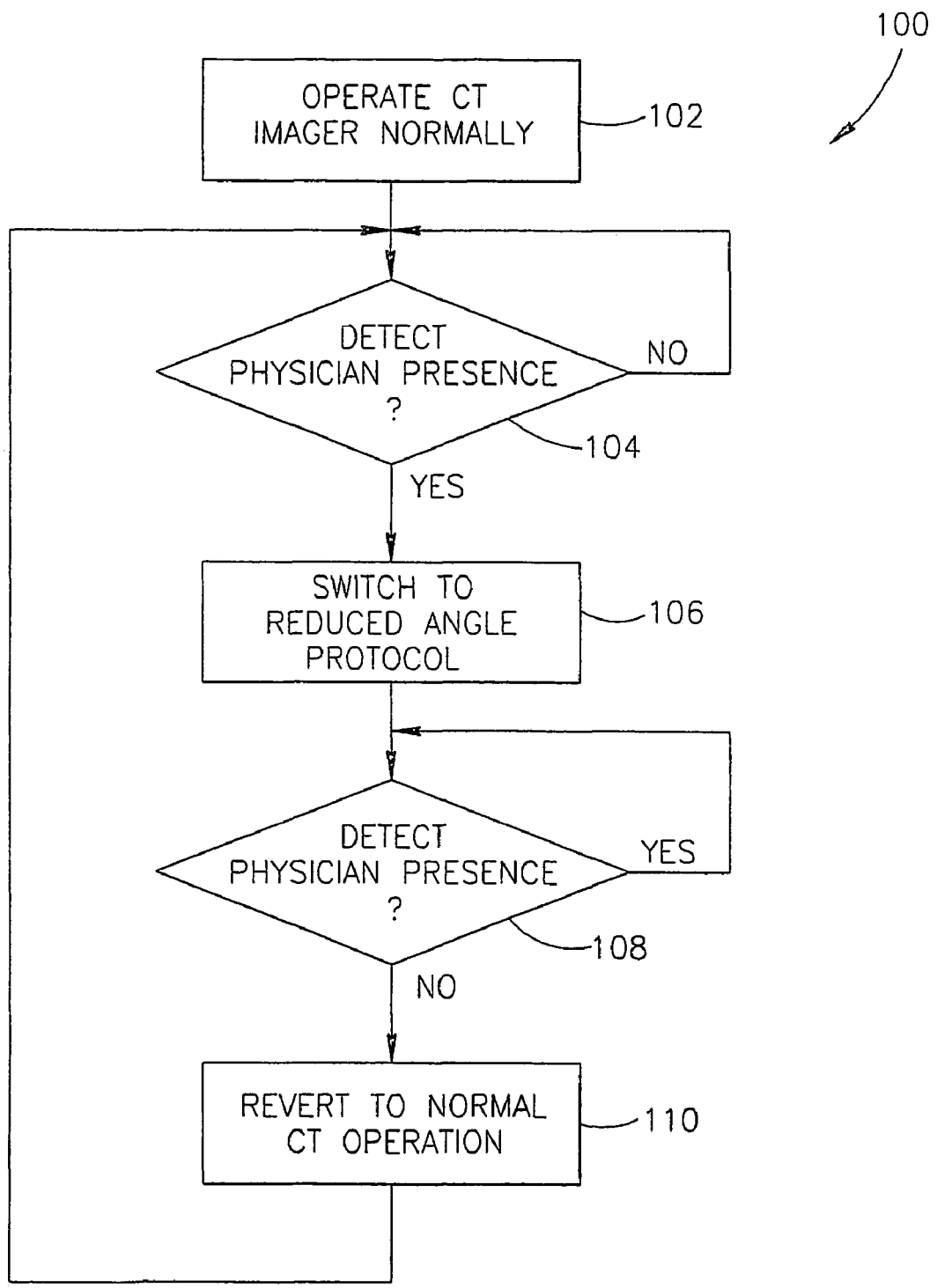
FIG. 3 shows a flow chart of the operation of a CT imager, in accordance with an embodiment of the invention.

FIG. 3 is a flow chart of a method 100 of reducing irradiation in accordance with an embodiment of the invention.

At 102, the CT imager is turned on and acquires images in the normal manner. At 104, the presence of the physician is detected and at 106, the imager switches to a reduced angle protocol. At 108, the absence of the physician is detected and the imager switches back to the normal acquisition mode (110).

Figure 4:
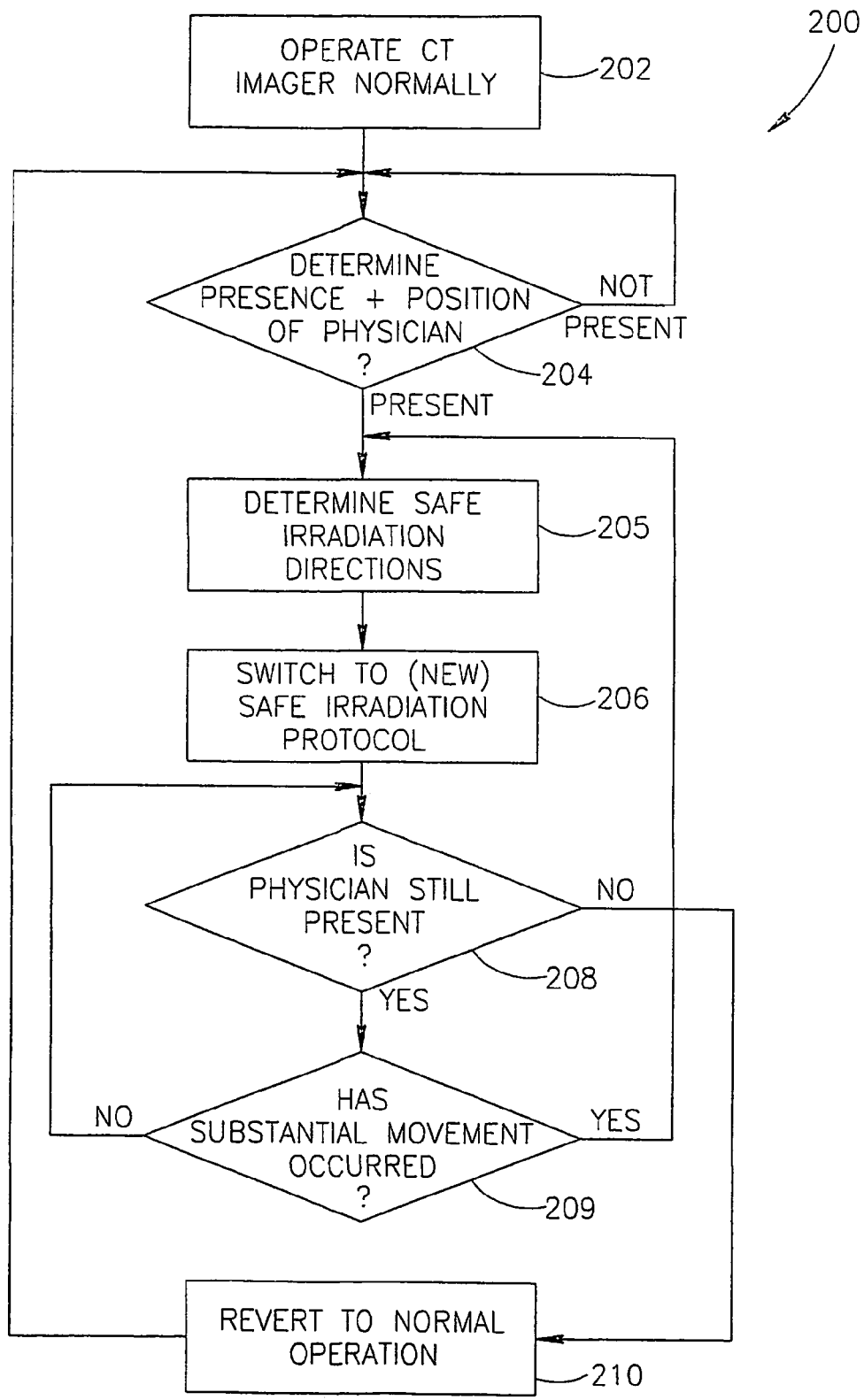
FIG. 4 shows a flow chart of an alternative embodiment of the invention.

FIG. 4 is a flow chart of a method 200 of reducing irradiation in accordance with an alternative embodiment of the invention.

At 202, the CT imager is turned on and acquires images in the normal manner. At 204, the presence and position of the physician is detected. At 205 controller 46 determines safe angles for irradiation and at 206, the imager switches to a reduced angle protocol having these angles. At 208 a determination is made of whether the physician is still-present. If he is not the system reverts to the normal protocol (210). If he is present, a determination (209) is made of whether he has moved substantially within the field. If he has, a new determination of a safe protocol is made (205) and the irradiation protocol is changed in response to it (206). If no substantial movement is detected, no change in the protocol is made.

The present invention has been described utilizing best mode embodiments thereof. However, variations of the embodiments described may be present in other embodiments of the invention. For example:
(1) the determinations of 208 and 209 may be combined into a single determination or may be reversed;
(2) the CT system may revert to normal operation or may remain in reduced angle irradiation operation;
(3) the imager may start out (202) in a predetermined reduced angle operation and only be updated by the determinations of presence and position;
(4) the determination of presence may be by a user input (pushbutton or footswitch); or
(5) as indicated above, the imager may not even detect the presence but operate in a reduced angle irradiation mode whenever an invasive procedure is contemplated.

Other variations on and combinations of the above described methods and apparatus, delete of steps or combinations of described methods are also possible, within the scope of the invention as claimed.

As used herein, the terms "have", "include" and "comprise" or their conjugates, mean "including but not limited to".

The invention claimed is:

1. A CT system for use in interventional procedures on a patient supported by a support surface, having:
   a radiation source which moves relative to the patient to irradiate the patient over an irradiation field;
   a radiation detector which detects radiation from the source;
   an imager which reconstructs raw data acquired by the detector into images of the patient;
   at least one presence detector operative to, indicate the presence of a person other than the patient in the irradiation field, the presence detector including an analysis circuitry which analyzes at least one of:
   the raw data acquired by the detector,
   the images reconstructed by the imager,
   projection data, and
   changes in an output from the detector;
   a control system which controls the radiation source to irradiate the patient in (1) a normal mode and (2) a reduced angle mode in which the patient is irradiated only from directions at which the other person is not indicated to be present in a radiation path between the radiation source and the patient, the control system switching from the normal mode to the reduced angle mode in response to said detection of the other person in the irradiation field.

2. A CT system according to claim 1 wherein the normal mode comprises irradiation of the patient mainly from beneath the support.

3. A CT system according to claim 2 where the normal mode also includes irradiating the patient from at least one side, to an extent necessary to acquire complete sets of data for image reconstruction.

4. The CT system according to any of claims 1–3 wherein said presence detector also determines a position of the other person in the irradiation field.

5. The CT system according to claim 1 wherein the analysis circuitry analyzes one of the raw data and the reconstructed images.

6. The CT system according to claim 1 wherein the analysis circuitry analyzes the projection data.

7. The CT system according to claim 1 wherein the presence detector further includes a source and a detector, wherein said presence is indicated based on a change in a signal produced by said detector.

8. The CT system according to claim 1 and wherein the presence detector further includes a physical indicator that switches the CT system between said modes.

9. A CT system comprising:
   a radiation source which rotates around a patient to irradiate the patient over an irradiation field;
   a radiation detector which detects radiation from the radiation source;
   an imager connected with the detector to reconstruct raw data acquired from the detector into CT images of the patient in the radiation field;
   analysis circuitry that analyzes one of CT images reconstructed by the imager and the raw data acquired by the imager to indicate the presence of a person other than the patient in the irradiation field;

a controller which controls the radiation source to irradiate the patient in (1) a normal mode over at least an angular segment of the irradiation field extending above the patient and (2) a reduced angle mode only over one or more angular segments of the irradiation field in which the other person is not indicated as being present, the controller switching between the normal and reduced angle modes in response to the analysis circuitry indicating the presence of the other person in the irradiation field.

10. A CT system including:
a patient support surface mounted to position a patient in an irradiation field;
a radiation source which supplies radiation to the irradiation field and which is mounted to rotate circumferentially around the patient;
an x-ray detector mounted to receive radiation from the radiation source that has passed through the patient;
a presence detector which determines a presence and position of a person other than the patient in the irradiation field;
a controller that receives presence and position information from the presence detector and controls the radiation source to operate in:
  a normal mode in which the patient is irradiated at least from above the support surface, and
  a reduced angle mode in which the radiation source is gated OFF over an angle of rotation in which the other person is indicated as being present in the irradiation zone,
the controller switching between the normal and reduced angle mode in response to detecting the presence of the other person in the irradiation field and selecting the OFF angle in accordance with the detected position of the other person in the irradiation field.

11. The CT system according to claim 1 wherein the normal mode comprises irradiating the patient circumferentially over 360 degrees.

12. A method of CT scanning using a CT scanner, for use in interventional procedures on a patient, which scanner includes a radiation source which irradiates the patient over a scanner field, a detector which detects radiation from the source, a support surface which supports the patient between the radiation source and the detector, and an imager that reconstructs an output of the detector into CT images, the method comprising:
analyzing one of the detector output, projection data, and the reconstructed CT images for an indication of the presence of a person other than the patient in the field of the scanner; and
switching the CT scanner between (1) a normal mode in which the patient is irradiated over an angle including irradiation from a general direction above the support surface, and (2) a reduced angle mode in which the patient is irradiated only from angle at which the other person is indicated as not being present or is assumed not to be present based on the analyzing step.

13. The method according to claim 12 wherein the reduced angle mode comprises irradiation of the patient mainly from beneath the support.

14. The method according to claim 13 where the reduced angle mode also includes irradiating the patient from at least one side, to an extent necessary to acquire complete sets of data for image reconstruction.

15. The method according to claim 13 wherein the reduced angle irradiation is based on a known intervention direction.

16. The method according to claim 12 wherein the analyzing step includes analyzing the CT images reconstructed by the imager.

17. The method according to claim 12 wherein determining the analyzing step includes analyzing raw data acquired by the imager from the detector.

18. The method according to claim 12 wherein the analyzing step includes analyzing the projection data.

19. The method according to claim 12 wherein the analyzing step includes determining a position of the other person in the scanner field.

20. The method according to claim 19 further including controlling the extent of the reduced angle responsive to a detected position of the other person in the scanner field.

* * * * *